(12) United States Patent
Tamezane et al.

(10) Patent No.: US 10,288,637 B2
(45) Date of Patent: May 14, 2019

(54) AUTOMATIC ANALYZER

(71) Applicant: HITACHI HIGH-TECHNOLOGIES CORPORATION, Tokyo (JP)

(72) Inventors: Hideto Tamezane, Tokyo (JP); Isao Yamazaki, Tokyo (JP); Masaharu Nishida, Tokyo (JP); Kumiko Kamihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 170 days.

(21) Appl. No.: 15/310,808

(22) PCT Filed: Apr. 22, 2015

(86) PCT No.: PCT/JP2015/062180
§ 371 (c)(1),
(2) Date: Nov. 14, 2016

(87) PCT Pub. No.: WO2015/174226
PCT Pub. Date: Nov. 19, 2015

(65) Prior Publication Data
US 2017/0089938 A1   Mar. 30, 2017

(30) Foreign Application Priority Data

May 15, 2014   (JP) .................................. 2014-101657

(51) Int. Cl.
*G01N 35/10* (2006.01)
*G01N 35/02* (2006.01)
(Continued)

(52) U.S. Cl.
CPC ...... *G01N 35/1009* (2013.01); *G01L 19/0092* (2013.01); *G01N 1/14* (2013.01);
(Continued)

(58) Field of Classification Search
CPC ............... G01N 35/1009; G01N 35/00; G01N 35/00732; G01N 35/025; G01N 35/10;
(Continued)

(56) References Cited

U.S. PATENT DOCUMENTS

2004/0034479 A1\* 2/2004 Shimase ............ G01N 35/1016
702/19
2009/0060785 A1\* 3/2009 Shimane ............... G01F 23/265
422/67
(Continued)

FOREIGN PATENT DOCUMENTS

JP       6-331630 A    12/1994
JP       11-258244 A    9/1999
(Continued)

OTHER PUBLICATIONS

International Preliminary Report on Patentability received in corresponding International Application No. PCT/JP2015/062180 dated Nov. 24, 2016.
(Continued)

*Primary Examiner* — Benjamin R Whatley
(74) *Attorney, Agent, or Firm* — Mattingly & Malur, PC

(57) ABSTRACT

A pressure signal process unit acquires data under a predetermined condition and a statistic distance between the acquired data and determination-purpose reference data stored in a storage unit is calculated. It is determined whether or not dispensing is abnormal and whether the determination-purpose reference data is suitable for an abnormality detection function to be properly fulfilled. If the determination-purpose reference data is not suitable for an abnormality detection function to be properly fulfilled, temporary determination-purpose reference data is prepared so as to be compared with the previously acquired data under a predetermined condition. If a difference therebetween is greater than a predetermined threshold value, a possibility
(Continued)

that an automatic analyzer may have an abnormal component or that a failure may occur in the automatic analyzer is determined, and the result is transmitted to cause a display device to display an alarm.

10 Claims, 13 Drawing Sheets

(51) Int. Cl.
  *G01N 35/00* (2006.01)
  *G01L 19/00* (2006.01)
  *G01N 1/14* (2006.01)
(52) U.S. Cl.
  CPC ....... *G01N 35/00* (2013.01); *G01N 35/00732* (2013.01); *G01N 35/025* (2013.01); *G01N 35/10* (2013.01); *G01N 2035/009* (2013.01); *G01N 2035/1018* (2013.01)
(58) Field of Classification Search
  CPC ..... G01N 2035/009; G01N 2035/1018; G01N 1/14; G01L 19/0092
  See application file for complete search history.

(56) References Cited

U.S. PATENT DOCUMENTS

| | | | |
|---|---|---|---|
| 2009/0169434 A1* | 7/2009 | Ogusu | G01N 35/1016 422/400 |
| 2010/0313687 A1* | 12/2010 | Ogusu | B01F 11/0071 73/864.11 |
| 2013/0121880 A1* | 5/2013 | Yamazaki | G01N 35/1016 422/81 |
| 2013/0130369 A1* | 5/2013 | Wilson | B01L 3/50825 435/289.1 |
| 2015/0323557 A1* | 11/2015 | Tamezane | G01N 35/1009 422/67 |

FOREIGN PATENT DOCUMENTS

| | | |
|---|---|---|
| JP | 2008-224691 A | 9/2008 |
| JP | 2013-24783 A | 2/2013 |
| JP | 2013-185912 A | 9/2013 |
| WO | 2013/106457 A1 | 7/2013 |
| WO | 2014/013836 A1 | 1/2014 |

OTHER PUBLICATIONS

International Search Report of PCT/JP2015/062180 dated Jul. 21, 2015.

Extended European Search Report received in corresponding European Application No. 1579281.4 dated Nov. 29, 2017.

* cited by examiner

[Fig. 1]
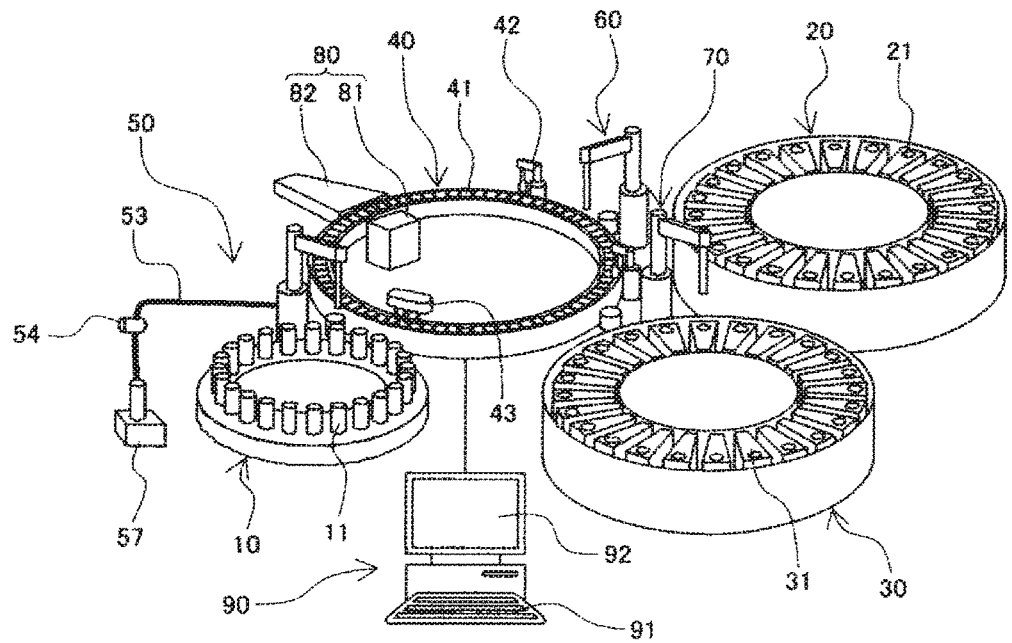
[Fig. 2]
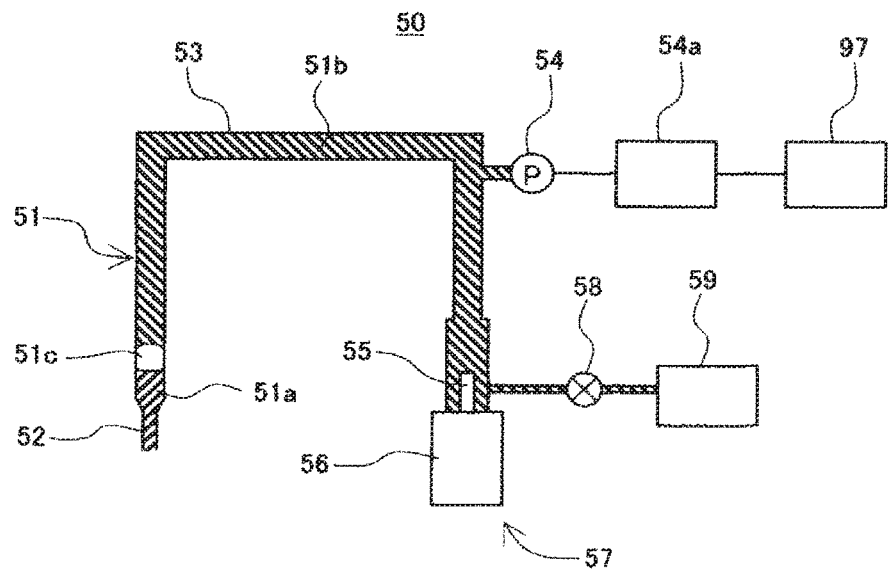

[Fig. 3]
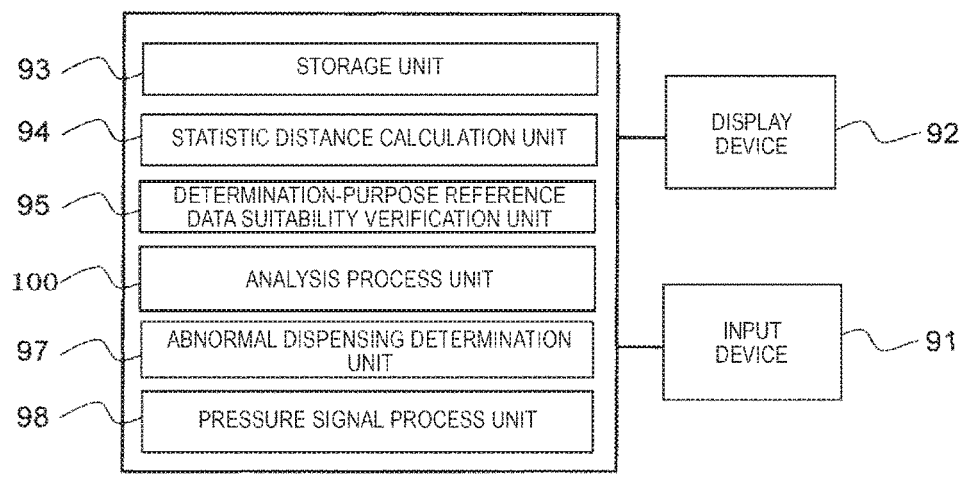
[Fig. 4]
| EVENT No. \ FEATURE VARIABLE No. | 1 | 2 | ... | k-1 | k |
|---|---|---|---|---|---|
| 1 | $X_{1,1}$ | $X_{1,2}$ | ... | $X_{1,k-1}$ | $X_{1,k}$ |
| 2 | $X_{2,1}$ | $X_{2,2}$ | ... | $X_{2,k-1}$ | $X_{2,k}$ |
| . | ... | ... | ... | ... | ... |
| n-1 | $X_{n-1,1}$ | $X_{n-1,2}$ | ... | $X_{n-1,k-1}$ | $X_{n-1,k}$ |
| n | $X_{n,1}$ | $X_{n,2}$ | ... | $X_{n,k-1}$ | $X_{n,k}$ |

[Fig. 5]
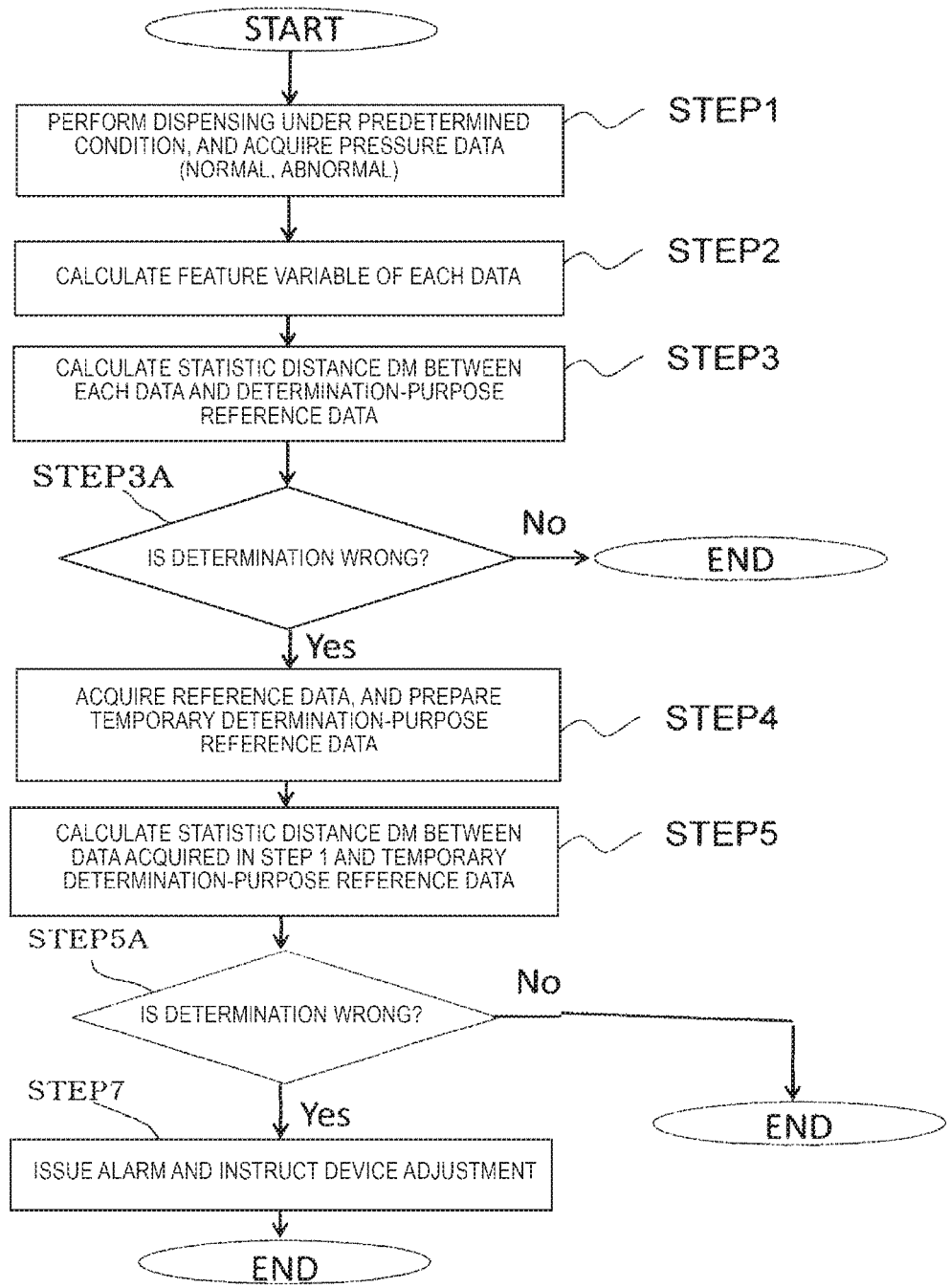

[Fig. 6]

| SEQUENCE NO. | CONDITION | SETTING AMOUNT (μL) | PSEUDO-REAGENT (ASPIRATING TARGET) | NUMBER OF ACQUISITION TIMES |
|---|---|---|---|---|
| 1 | NORMAL | 10 | PURE WATER | 5 |
| 2 | NORMAL | 10 | AQUEOUS SOLUTION CONTAINING GLYCERIN 30% | 5 |
| 3 | ABNORMAL (AIR ASPIRATING) | 10 | — | 5 |
| 4 | NORMAL | 49 | PURE WATER | 5 |
| 5 | NORMAL | 49 | AQUEOUS SOLUTION CONTAINING GLYCERIN 30% | 5 |
| 6 | ABNORMAL (AIR ASPIRATING) | 49 | — | 5 |
| 7 | NORMAL | 50 | PURE WATER | 5 |
| 8 | NORMAL | 50 | AQUEOUS SOLUTION CONTAINING GLYCERIN 30% | 5 |
| 9 | ABNORMAL (AIR ASPIRATING) | 50 | — | 5 |
| 10 | NORMAL | 100 | PURE WATER | 5 |
| 11 | NORMAL | 100 | AQUEOUS SOLUTION CONTAINING GLYCERIN 30% | 5 |
| 12 | ABNORMAL (AIR ASPIRATING) | 100 | — | 5 |

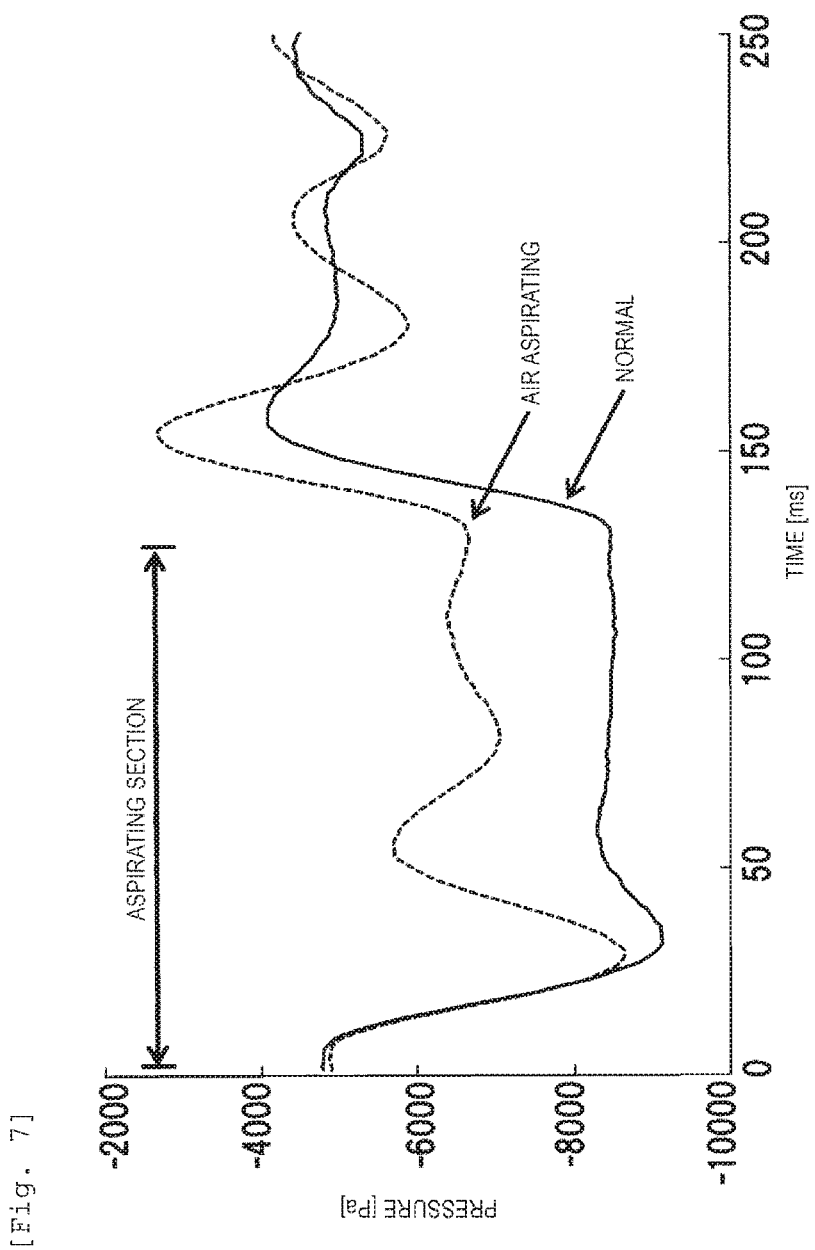
[Fig. 7]

[Fig. 8]
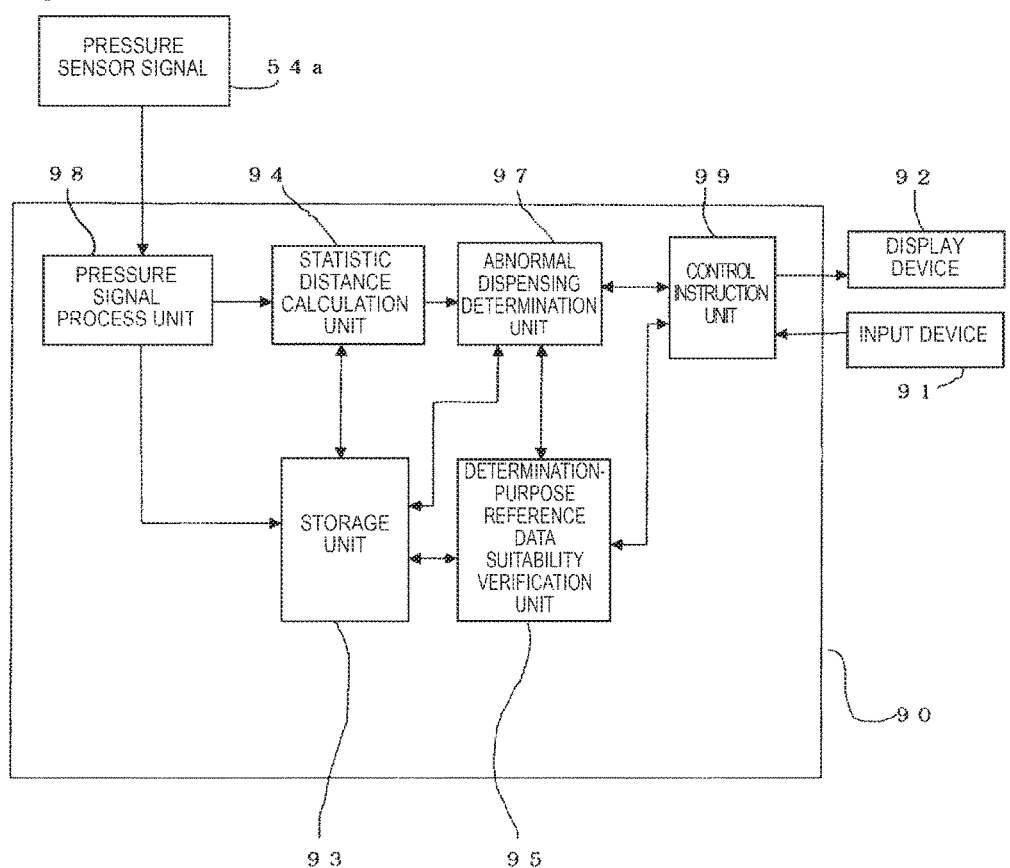

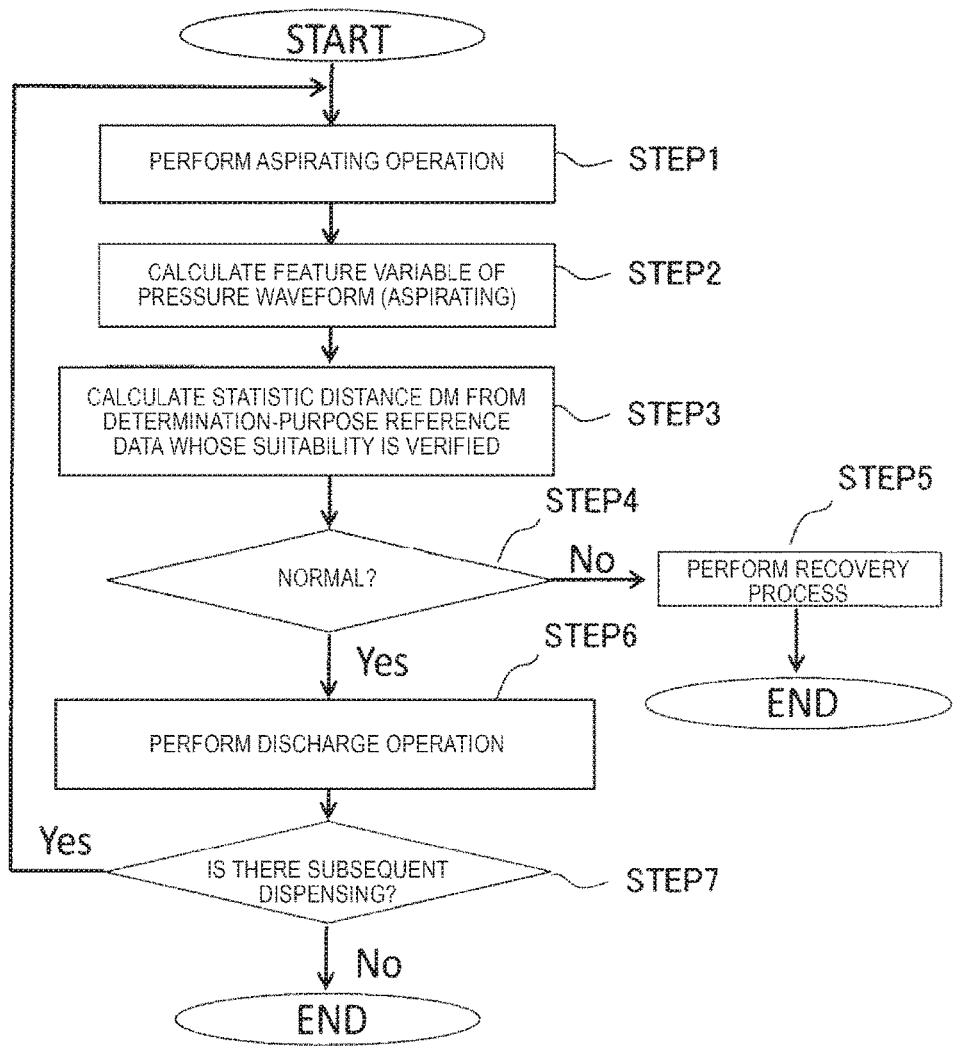
[Fig. 9]

[Fig. 10]
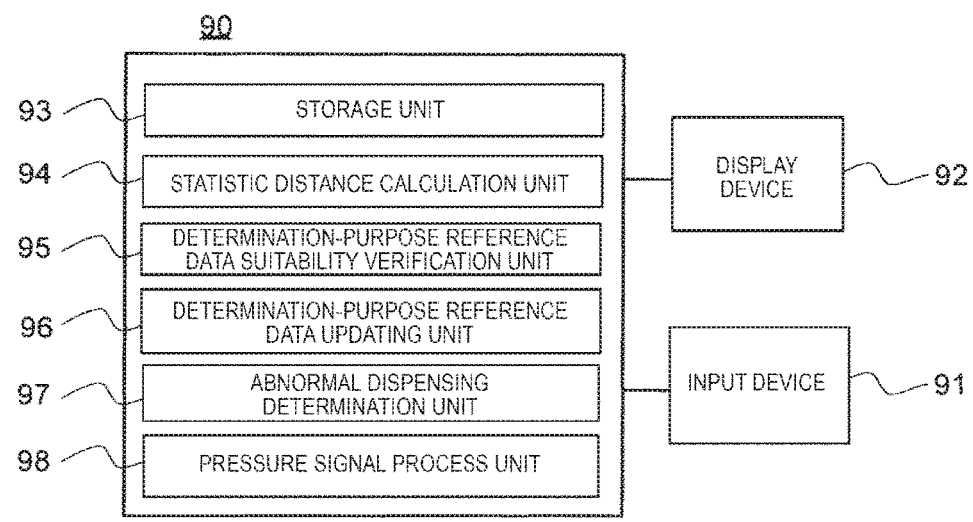

[Fig. 11]
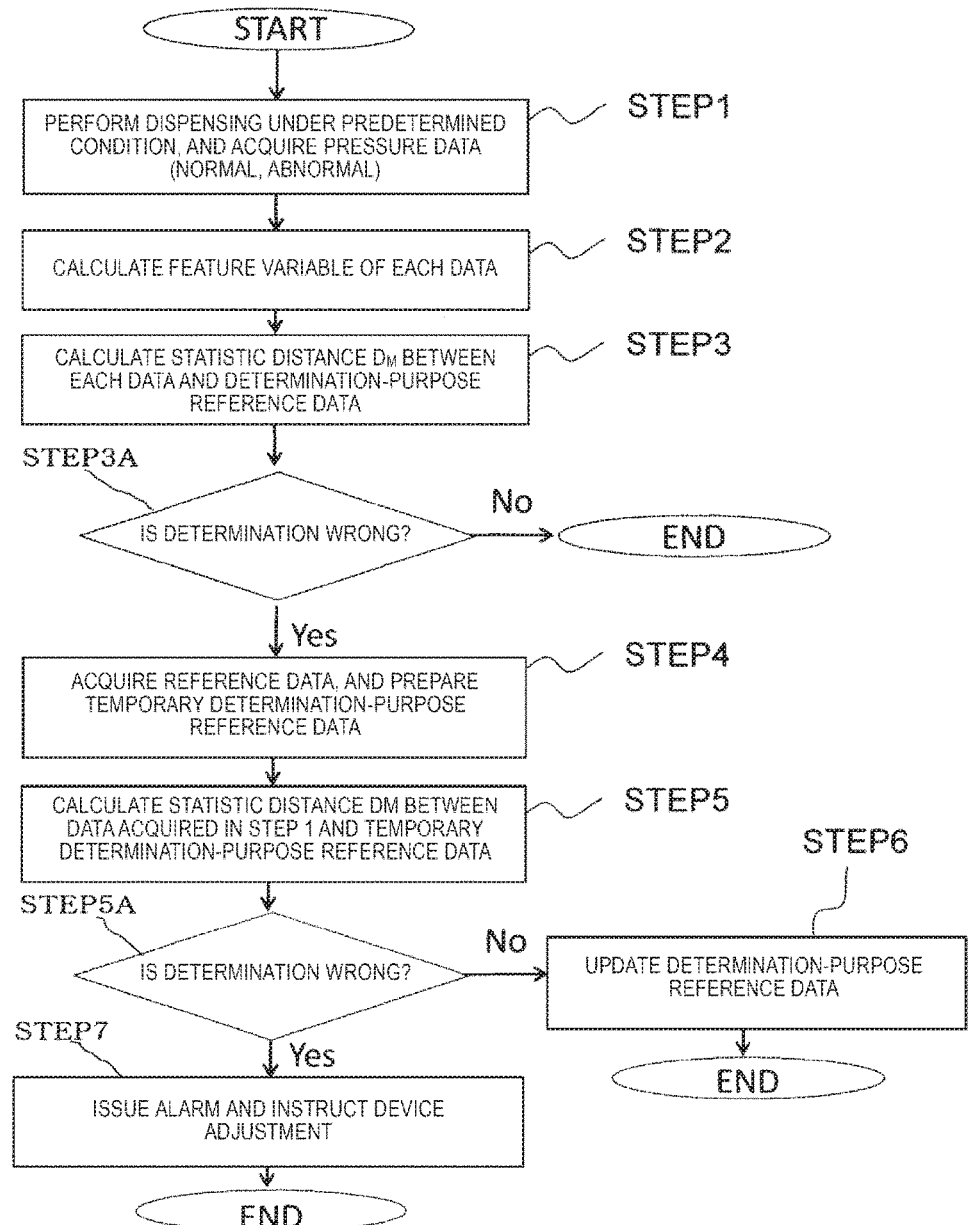

[Fig. 12]
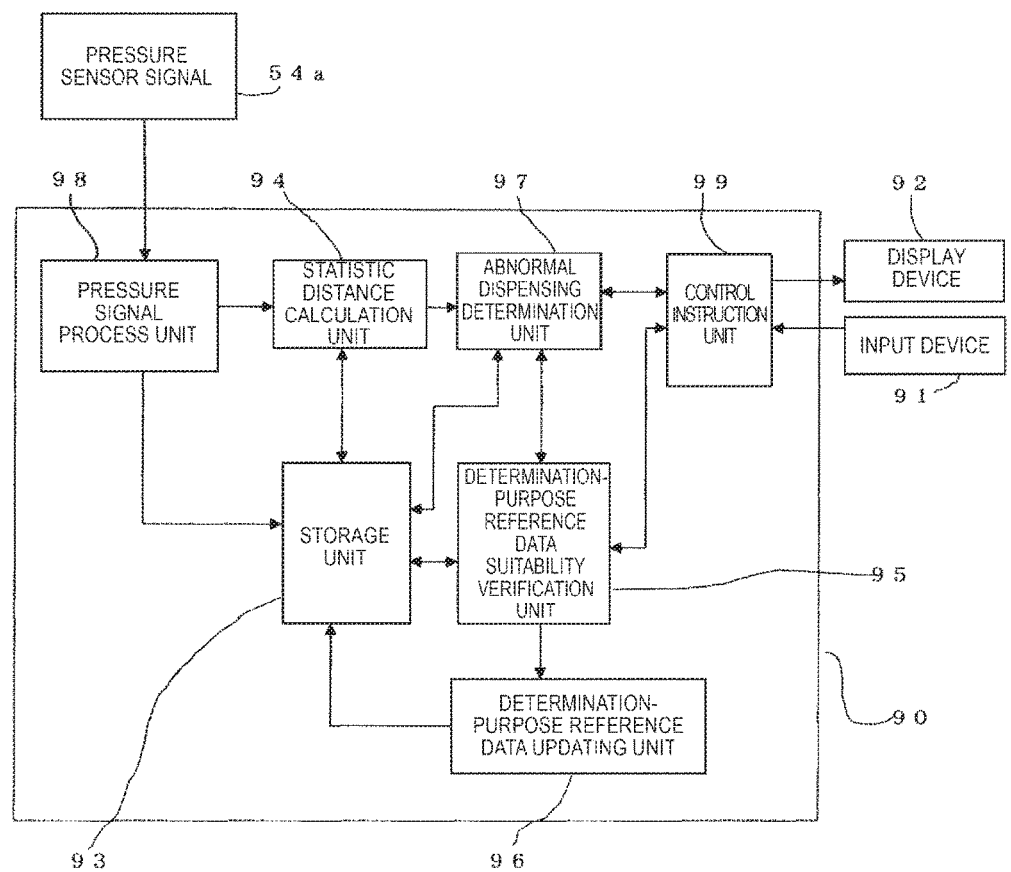

[Fig. 13]
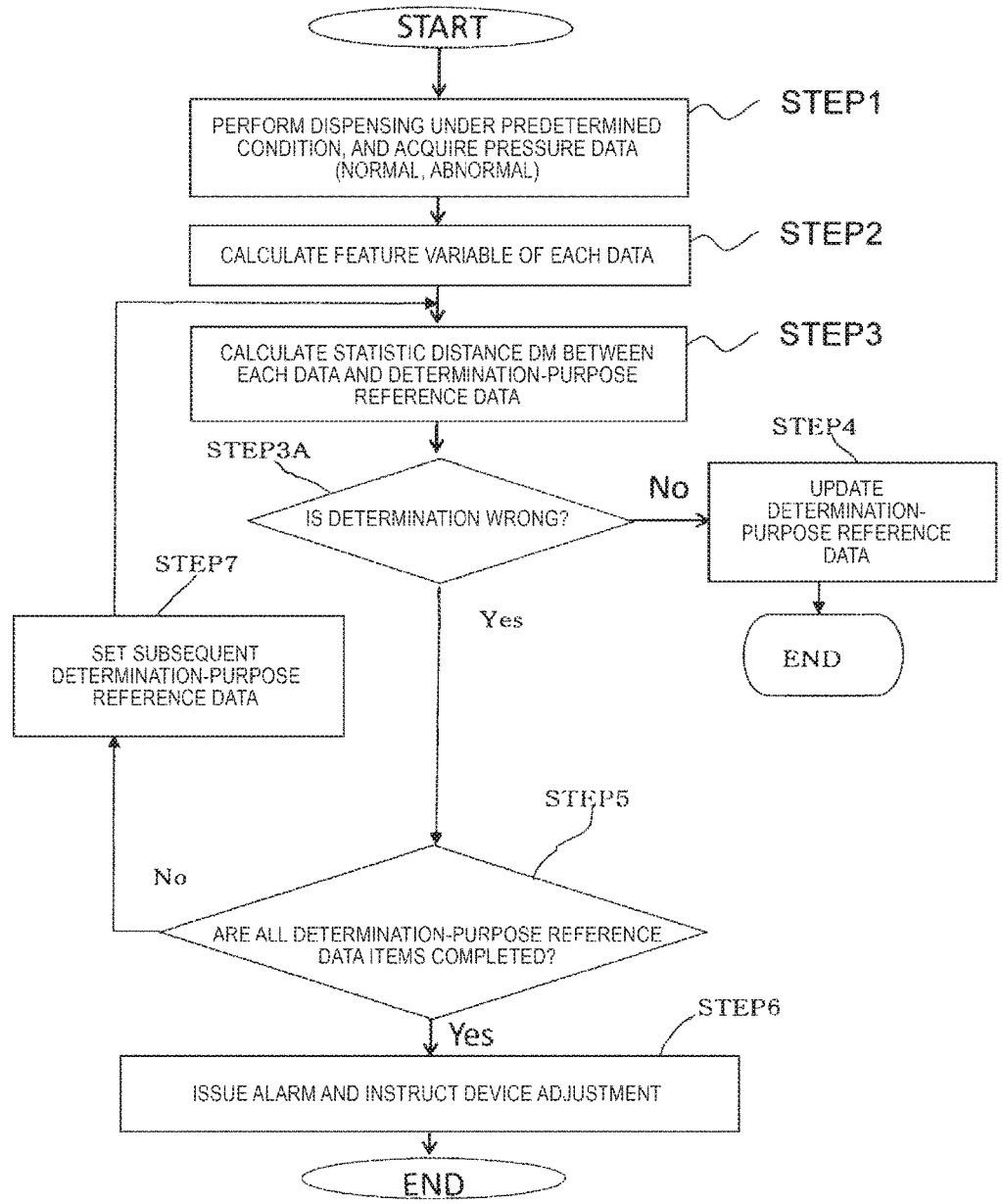

[Fig. 14]
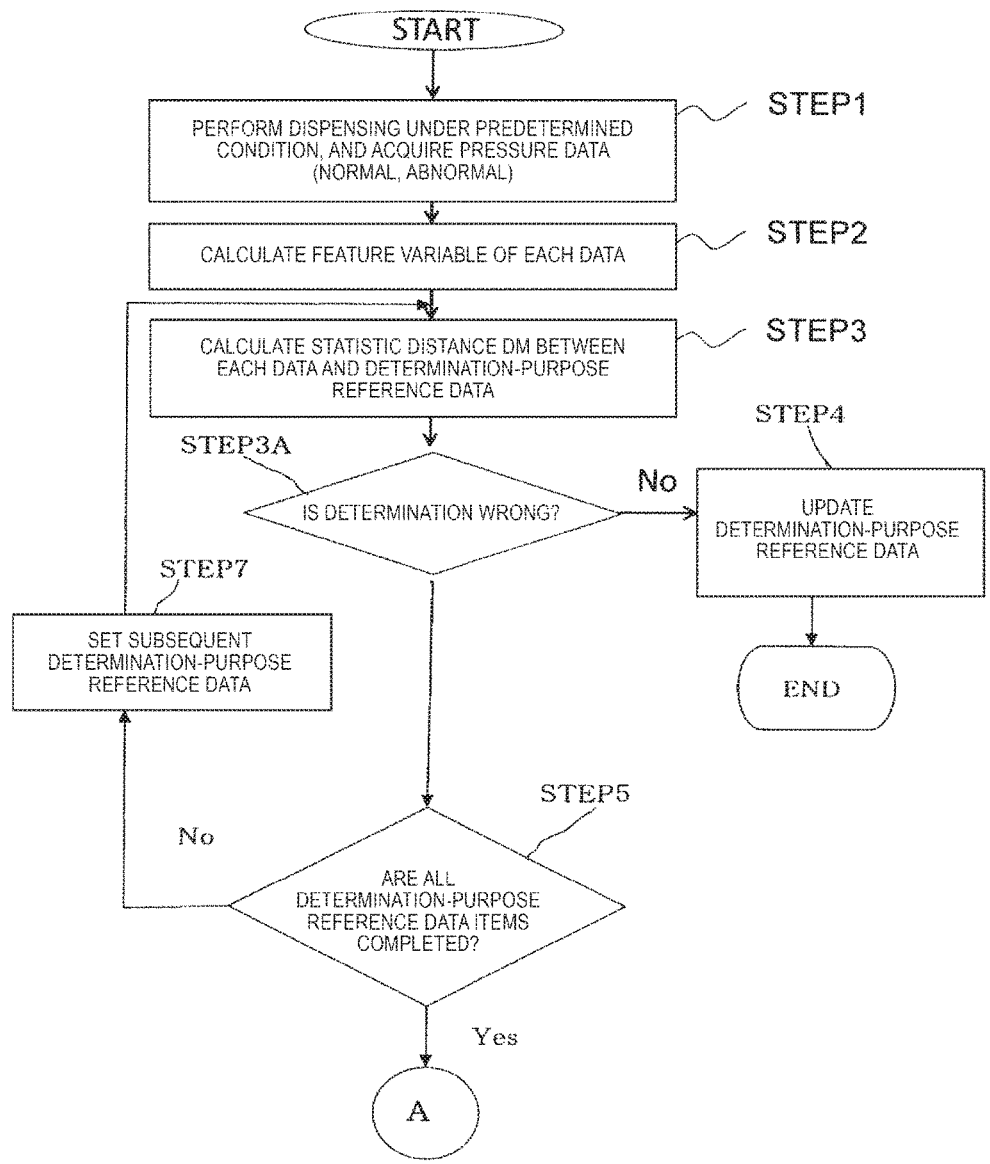

[Fig. 15]
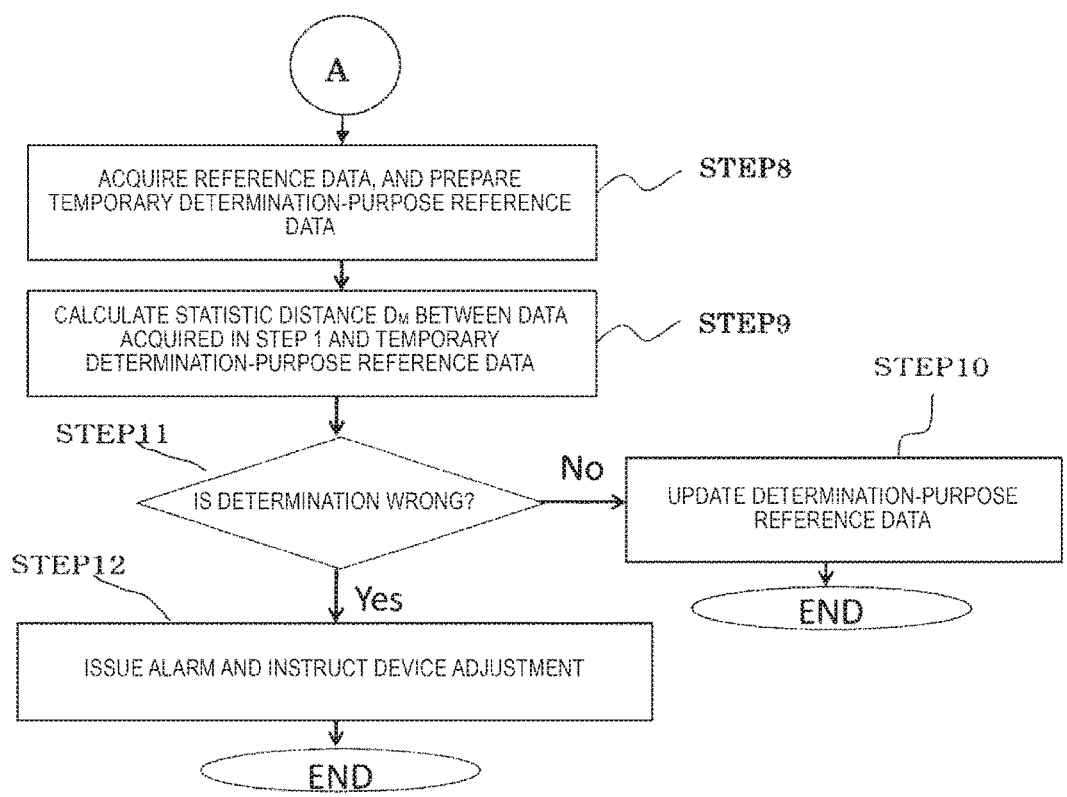

AUTOMATIC ANALYZER

TECHNICAL FIELD

The present invention relates to an automatic analyzer which performs qualitative/quantitative analysis on a living body specimen such as blood or urine.

BACKGROUND ART

An automatic analyzer performs qualitative/quantitative analysis by adding a reagent specifically reacting to a specific ingredient contained in a living body specimen (hereinafter, referred to as a specimen) such as blood or urine, by causing the reagent to react therewith, and by measuring optical density or an emitted light quantity of reaction liquid.

According to this automatic analyzer, in order to cause the specimen and the reagent to react with each other, it is necessary to provide a step of dispensing the specimen which is an analysis target contained in a specimen container or the reagent which is added to and reacted with the specimen, into a reaction container. A small amount of the specimen or the reagent is dispensed into the reaction container. Accordingly, accurate dispensing inevitably affects accurate analysis.

Therefore, it is important to reliably detect abnormal dispensing which may lead to inaccurate dispensing.

In a step of dispensing the specimen into the reaction container, factors frequently leading to abnormal dispensing include probe clogging in a probe which is caused by aspirating solid substances such as fibrin. If clogging occurs in the probe, a predetermined amount of specimen cannot be dispensed into the reaction container, and thus it is not possible to obtain reliable analysis results. In addition, in a case where air bubbles or liquid films are present on a liquid level of a test specimen, the air bubbles or the liquid films are determined as the liquid level. Consequently, an originally planned amount of the specimen cannot be aspirated, thereby causing the abnormal dispensing. In order to avoid the abnormal dispensing in a case where the air bubbles or the liquid films are present, it is conceivable to increase the amount of the probe dipped into the test specimen. However, if the amount of the probe dipped into the test specimen increases, there is a possibility of increasing contamination and adversely affected analysis results.

Therefore, in order to minimize a depth of the probe dipped into the liquid as much as possible, an operation control method is generally employed in which the liquid level of the liquid inside the container is detected, a lowering operation of the probe is stopped at a position where a tip of the probe reaches slightly below the liquid level, and then, a predetermined amount of liquid is aspirated into the probe.

As means for detecting the liquid level of the test specimen, the most generally used one is an electrostatic capacity variation method of detecting variations in electrostatic capacity when the probe comes into contact with the liquid level.

However, as described above, in a case where a liquid level sensor is used in this way, if the air bubbles or the liquid films are present on the liquid level, these may be erroneously detected as the liquid level, thereby causing the abnormal dispensing.

In a step of dispensing the reagent into the reaction container, the abnormal dispensing is also caused to occur by aspirating the air bubbles generated on the liquid level of the reagent. If the amount of the probe dipped into the reagent increases similarly to a case of the specimen, there is a possibility of increasing contamination and adversely affected analysis results. Therefore, similarly to the case of the specimen, a probe operation control method is generally employed.

For example, as a technique of detecting the abnormal dispensing, PTL 1 discloses an automatic analyzer including at least one pressure sensor that detects pressure inside a dispensing channel connecting a probe which aspirates and discharges a sample and a dispensing syringe which generates the pressure for causing the probe to aspirate and discharge the sample, pressure value storage means for storing time-series output values of the pressure sensor during a sample dispensing operation, and storage means for storing a reference database having the time-series output values of the pressure sensor when the probe normally aspirates or discharges the sample.

Then, the automatic analyzer disclosed in PTL 1 above calculates the Mahalanobis distance from comparison data and the reference database which are prepared based on the time-series pressure sensor output values stored in the pressure value storage means, and determines the abnormal dispensing of the sample by comparing the calculation result with a predetermined threshold value.

CITATION LIST

Patent Literature

PTL 1: JP-A-2008-224691

SUMMARY OF INVENTION

Technical Problem

However, the above-described technique in the related art has the following problem.

In some cases, due to a time-dependent change (wear of a sealing piece) or replacement of each component configuring a channel, the output values of the pressure sensor installed inside the dispensing channel fluctuate even if the same specimen or the same reagent is dispensed. In a case where a fluctuation width is large, the reference database stored in advance is determined as unsuitable through abnormal dispensing detection in the device, thereby resulting in a problem in that detection performance becomes poor.

However, an operator or a service engineer has no means for verifying whether the abnormal dispensing detection performance is normally maintained and no means for dealing with poor performance.

Therefore, in spite of a state where component replacement or device adjustment is required, the operator or the service engineer cannot detect the state. Consequently, there is a possibility that analysis accuracy may be degraded.

The present invention is made in view of the above-described problem, and an object thereof is to provide an automatic analyzer which can accurately detect a state where component replacement or device adjustment is required, without being affected by a time-dependent change or replacement of each component configuring a channel.

Solution to Problem

In order to achieve the above-described object, the present invention is configured as follows.

According to the present invention, there is provided an automatic analyzer including a dispensing mechanism that dips a dispensing nozzle in a dispensing target contained in a container, and that aspirates and discharges the dispensing target to a reaction container, a pressure sensor that detects pressure inside the dispensing nozzle of the dispensing mechanism, an analysis process unit that analyzes a specimen contained in the reaction container, a storage unit that stores determination-purpose reference data used in determining whether the dispensing mechanism is normal or abnormal, an abnormal dispensing determination unit that determines whether or not a dispensing operation of the dispensing mechanism is abnormal, based on the determination-purpose reference data stored in the storage unit, a determination-purpose reference data suitability verification unit that verifies whether or not the determination-purpose reference data is suitable for abnormality detection, a control instruction unit that controls each operation of the dispensing mechanism, the pressure sensor, the analysis process unit, the abnormal dispensing determination unit, and the determination-purpose reference data suitability verification unit, and a display unit.

Then, in a case where the determination-purpose reference data suitability verification unit determines that the determination-purpose reference data is not suitable for the abnormality detection, the control instruction unit acquires temporary determination-purpose reference data, the determination-purpose reference data suitability verification unit determines whether or not the temporary determination-purpose reference data is suitable for the abnormality detection, and in a case where the determination-purpose reference data suitability verification unit determines that the temporary determination-purpose reference data is not suitable for the abnormality detection, the control instruction unit causes the display unit to display an alarm.

Advantageous Effects of Invention

According to the present invention, it is possible to realize an automatic analyzer which can accurately detect a state where component replacement or device adjustment is required, without being affected by a time-dependent change or replacement of each component configuring a channel.

BRIEF DESCRIPTION OF DRAWINGS

FIG. 1 is a view briefly illustrating an overall configuration of an automatic analyzer according to Embodiment 1 of the present invention.

FIG. 2 is a view schematically illustrating an internal configuration of a sample dispensing mechanism 50 as a representative of multiple dispensing mechanisms.

FIG. 3 is a functional block diagram illustrating details of a control device according to Embodiment 1.

FIG. 4 is a view illustrating an example of determination-purpose reference data used in order to calculate the Mahalanobis distance.

FIG. 5 is a flowchart with regard to a series of processes in the control device according to Embodiment 1.

FIG. 6 is a view illustrating an example of operation conditions for acquiring normal and abnormal data which are used for suitability verification of the determination-purpose reference data in STEP 1 in FIG. 5.

FIG. 7 illustrates an acquired waveform example of channel inner pressure data in normal and abnormal conditions which are used for verifying suitability of the determination-purpose reference data in STEP 1 in FIG. 5.

FIG. 8 is an internal configuration block diagram of the control device according to Embodiment 1, and is a view clearly illustrating a relationship of transmitting an instruction signal and data between internal configuration elements illustrated in FIG. 3.

FIG. 9 is an operation flowchart illustrating an abnormality determination process of a dispensing mechanism during an analysis process operation.

FIG. 10 is a functional block diagram illustrating details of a control device according to Embodiment 2.

FIG. 11 is a flowchart with regard to a series of processes in the control device according to Embodiment 2.

FIG. 12 is an internal configuration block diagram of the control device according to Embodiment 2, and is a view clearly illustrating a relationship of transmitting an instruction signal and data between internal configuration elements illustrated in FIG. 10.

FIG. 13 is a flowchart with regard to a series of processes in a control device according to Embodiment 3.

FIG. 14 is a flowchart with regard to a series of processes in a control device according to Embodiment 4.

FIG. 15 is a flowchart with regard to a series of processes in the control device according to Embodiment 4.

DESCRIPTION OF EMBODIMENTS

Hereinafter, embodiments according to the present invention will be described with reference to the drawings.

EMBODIMENTS

Embodiment 1

Embodiment 1 according to the present invention will be described.

(1) Overall Configuration of Automatic Analyzer

FIG. 1 is a view briefly illustrating an overall configuration of an automatic analyzer according to Embodiment 1 of the present invention.

Referring to FIG. 1, the automatic analyzer includes a sample disk (sample disk) 10, a first reagent disk 20, a second reagent disk 30, a reaction disk 40, a sample dispensing mechanism 50, a first reagent dispensing mechanism 60, a second reagent dispensing mechanism 70, a photometric mechanism 80, and a control device 90.

The sample disk 10 has multiple specimen containers 11 which are mounted thereon side by side in the circumferential direction, and which contain a specimen such as blood or urine serving as an analysis target. The sample disk 10 is rotatably driven by a rotary driving device (not illustrated), and conveys the specimen containers 11 in the circumferential direction.

The first reagent disk 20 has multiple reagent containers 21 which are mounted thereon side by side in the circumferential direction, and which contain a reagent (first reagent) used in analyzing the specimen. The first reagent disk 20 is rotatably driven in the circumferential direction by a rotary driving device (not illustrated), and conveys the reagent containers 21 in the circumferential direction.

The second reagent disk 30 has multiple reagent containers 31 which are mounted thereon side by side in the circumferential direction, and which contain a reagent (second reagent) used in analyzing the specimen. The second reagent disk 30 is rotatably driven in the circumferential direction by a rotary driving device (not illustrated), and conveys the reagent containers 31 in the circumferential direction.

The reaction disk 40 has multiple reaction containers 41 which are mounted thereon side by side in the circumferential direction, and which contain a liquid mixture (reaction liquid) of the specimen and the reagent. The reaction disk 40 is rotatably driven in the circumferential direction by a rotary driving device (not illustrated), and conveys the reaction containers 41 in the circumferential direction. In addition, a stirring mechanism 42 which stirs the liquid mixture contained in the reaction containers 41 and a cleaning mechanism 43 which cleans the reaction containers 41 whose analysis is completed are arranged on a conveyance route of the reaction containers 41 of the reaction disk 40.

The sample dispensing mechanism 50 dips a dispensing nozzle 51 (refer to FIG. 2 below) in the dispensing target specimen contained in the specimen container 11. The sample dispensing mechanism 50 aspirates the specimen, and discharges the specimen to the reaction container 41, thereby dispensing the specimen. The sample dispensing mechanism 50 is driven in the horizontal direction and in the vertical direction by a drive mechanism (not illustrated).

The first reagent dispensing mechanism 60 dips a dispensing nozzle (not illustrated) in the first dispensing target reagent contained in the reagent container 21. The first reagent dispensing mechanism 60 aspirates the first reagent, and discharges the first reagent to the reaction container 41, thereby dispensing the first reagent. The first reagent dispensing mechanism 60 is driven in the horizontal direction and in the vertical direction by a drive mechanism (not illustrated).

The second reagent dispensing mechanism 70 dips a dispensing nozzle (not illustrated) in the second dispensing target reagent contained in the reagent container 31. The second reagent dispensing mechanism 70 aspirates the second reagent, and discharges the second reagent to the reaction container 41, thereby dispensing the second reagent. The second reagent dispensing mechanism 70 is driven in the horizontal direction and in the vertical direction by a drive mechanism (not illustrated).

The photometric mechanism 80 is arranged on the conveyance route of the reaction container 41 in the reaction disk 40, and includes a light source 81 which emits light to the reaction container 41 containing a measurement target reaction liquid and a spectroscopic detector 82 which detects transmitted light transmitted through the reaction liquid contained in the reaction container 41. The detection result in the spectroscopic detector 82 is converted into a digital signal, and is sent to the control device 90.

The control device 90 controls overall operations of the automatic analyzer including each drive mechanism, and controls an analysis process for analyzing the specimen such as blood or urine serving as the analysis target and an abnormality determination process for determining abnormality of the respective dispensing mechanisms 50, 60, and 70 in response to the analysis process. The control device 90 includes an input device 91 for inputting various setting values or instructions and a display device 92 for displaying various setting screens or analysis result screens.

(1-1) Dispensing Mechanisms 50, 60, and 70

FIG. 2 is a view schematically illustrating an internal configuration of the sample dispensing mechanism 50 as a representative of multiple dispensing mechanisms.

As illustrated in FIG. 2, the sample dispensing mechanism 50 includes the dispensing nozzle 51 having a dispensing channel 53 through the inside of which a specimen 51*a* and a system liquid 51*b* pass, a metering pump 57 which aspirates and discharges the sample 51*a*, the system liquid 51*b*, and separated air 51*c* with respect to the dispensing nozzle 51, a pressure sensor 54 which detects pressure inside the dispensing nozzle 51 (in other words, inside the dispensing channel 53), a pump 59 which is connected to the dispensing channel 53, and a valve 58 which is disposed in a channel between the dispensing channel 53 and the pump 59.

A throttle portion 52 whose cross-sectional area is small in the dispensing channel 53 is disposed in one end on a side of the dispensing nozzle 51 which is dipped in the reagent.

The metering pump 57 is connected to the other end of the dispensing nozzle 51. A drive mechanism 56 causes a plunger 55 to enter the inside of the dispensing channel 53, or causes the plunger 55 to retreat from the inside of the dispensing channel 53. In this manner, the metering pump 57 adjusts capacity inside the dispensing channel 53, thereby aspirating and discharging the specimen through the throttle portion 52.

The pump 59 supplies the system liquid 51*b* to a dispensing route 53, and is controlled together with open and closed states of the valve 58 by the control device 90.

The detection result of the pressure sensor 54 is sent to the control device 90 via an A/D converter 54*a*. The first and second reagent dispensing mechanisms 60 and 70 also have the same configuration as the sample dispensing mechanism 50, and thus detailed description thereof will be omitted.

(1-2) Control Device 90

FIG. 3 is a functional block diagram illustrating details of the control device 90.

Referring to FIG. 3, in addition to the input device 91 and the display device 92, the control device 90 includes various functional blocks such as a pressure signal process unit 98 that calculates feature variables in a digital signal of a pressure signal from the A/D converter 54*a* in the respective dispensing mechanisms 50, 60, and 70, a storage unit 93 that stores various information items used in operations of the automatic analyzer such as the analysis process or the abnormality determination process, a statistic distance calculation unit 94 that calculates a statistic distance which is an index obtained by quantifying similarity between two events represented by multiple feature variables, a determination-purpose reference data suitability verification unit 95 that verifies whether the determination-purpose reference data stored in the storage unit 93 in order to be used in the abnormality determination process of the dispensing process is suitable for accurate abnormality detection, an abnormal dispensing determination unit 97 that performs the abnormality determination process of the dispensing process by using the determination-purpose reference data which is verified as suitable determination-purpose reference data through the determination-purpose reference data suitability verification unit 95 and the determination-purpose reference data updating unit 96, and an analysis process unit 100 that analyzes the specimen such as blood or urine serving as the analysis target.

Although not illustrated in FIG. 3, the control device 90 includes a control instruction unit 99 (to be described later) that controls the reaction disk 40, the first reagent disk 20, the second reagent disk 30, the sample disk 10, the dispensing mechanism 50, 60, 70, and the photometric mechanism 80.

(2) Analysis Process

Next, a basic operation in an analysis process of the automatic analyzer according to Embodiment 1 will be described.

In the analysis process, qualitative/quantitative analysis is performed by adding a reagent specifically reacting to a specific ingredient contained in the specimen such as blood or urine, by causing the reagent to react therewith, and by measuring optical density of the reaction liquid.

First, an analysis target specimen (sample) is contained in the specimen container 11, and the specimen container 11 is mounted on the sample disk 10. Information (analysis items, types of reagent, or the like) required for the analysis process of each specimen is input by the input device 91 and is stored in the control device 90 in advance.

Next, a certain amount of specimen is aspirated from the specimen container 11 by using the dispensing probe 51 of the sample dispensing mechanism 50, and is discharged to the reaction container 41 mounted on the reaction disk 40, thereby performing dispensing.

Subsequently, a determined amount of reagent is aspirated from the reagent containers 21 and 31 by using the first and second reagent dispensing mechanisms 60 and 70, and is discharged to the reaction container 41 of the reaction disk 40, thereby performing dispensing and causing the stirring mechanism 42 to performing stirring. A type, amount, or timing of the reagent to be dispensed by the first and second reagent dispensing mechanisms 60 and 70 is determined in advance depending on a type or analysis items of the specimen.

Subsequently, the reaction disk 40 is periodically and repeatedly rotated and stopped. Photometry is performed at a timing when the reaction container 41 passes the photometric mechanism 80 (that is, between the light source 81 and the spectroscopic detector 82). The photometry is repeatedly performed by the spectroscopic detector 82 during a predetermined reaction time period. Thereafter, the cleaning mechanism 43 cleans the reaction container 41 which completes analysis. The photometry is also performed on the multiple specimen containers 41 in parallel by the photometric mechanism 80. The detection result obtained by the photometric mechanism 80 is sent to the control device 90, concentration of the ingredient is calculated depending on a type of the analysis, and is displayed on the display device 92.

(2-1) Dispensing Process

Next, a basic operation of the dispensing operation performed by the dispensing mechanism in the analysis process will be described.

Herein, the sample dispensing mechanism 50 will be described as a representative of the dispensing mechanisms 50, 60, and 70.

In the dispensing process (that is, dispensing process of the specimen) performed by the sample dispensing mechanism 50, in a state where the dispensing probe 51 is dipped in the specimen which is a dispensing target, the specimen is aspirated and discharged to the predetermined reaction container 41, thereby performing the dispensing.

Before the specimen is aspirated, the control device 90 first opens the valve 58, fills the inside of the dispensing channel 53 of the dispensing probe 51 with the system liquid 51b supplied from the pump 59, and closes the valve 58. Then, in a state where a distal end of the dispensing probe 51 is located in the air, the drive mechanism 56 operates the plunger 55 to be lowered, and the separated air 51c is aspirated.

Next, the dispensing probe 51 is lowered into the specimen container 11. In a state where the distal end is dipped in the specimen, the plunger 55 is further operated to be lowered. The specimen is aspirated into the throttle portion 52 and the dispensing channel 53 of the dispensing probe 51. Thereafter, in a state where the dispensing probe 51 is moved onto the reaction container 41, the drive mechanism 56 operates the plunger 55 to be raised, and the specimen is discharged until the specimen reaches the separated air 51c.

Pressure of the dispensing channel 53 of the dispensing probe 51 when the dispensing probe 51 aspirates and discharges the specimen is detected by the pressure sensor 54. The pressure is converted into a digital signal by the A/D converter 54a, and the digital signal is sent to the control device 90. The control device 90 performs an abnormality determination process for determining whether or not the respective dispensing mechanisms 50, 60, and 70 are abnormal, based on the detection result of the pressure sensor 54 (that is, a pressure waveform during the aspirating and the discharging). In a case where it is determined that there is abnormality, the analysis process is temporarily stopped, and causes the display device 92 to display an alarm. In this manner, an operator is notified of the alarm so as to urge a recovery operation.

As the recovery operation, any one among re-dispensing after removing a cause of abnormality occurrence, performing analysis on another specimen, stopping the device, and the like may be selected.

After discharging the specimen, the dispensing probe 51 is cleaned by the system liquid 51b flowing in response to opening and closing of the valve 58, and is provided for the subsequent dispensing process.

(2-2) Abnormality Determination Process

Next, the abnormality determination process will be described.

The abnormality determination process is a process for determining whether the respective dispensing mechanisms 50, 60, and 70 are abnormal during the dispensing process.

In the abnormality determination process, the statistic distance calculation unit 94 acquires a pressure waveform (that is, the detection result of the pressure sensor 54) when each dispensing nozzle of the respective dispensing mechanisms 50, 60, and 70 aspirates and discharges a target (specimen or reagent), and calculates a statistic distance by using the determination-purpose reference data which is stored in the storage unit 93 and whose suitability is verified in advance so that the abnormality detection normally functions.

In Embodiment 1, a case where the Mahalanobis distance is employed as the statistic distance used in the statistic distance calculation unit 94 will be described as an example.

The abnormal dispensing determination unit 97 compares the statistic distance calculated by the statistic distance calculation unit 94 with a threshold value stored in the storage unit 93, and determines abnormal dispensing of the respective dispensing mechanisms 50, 60, and 70, based on the comparison result. The threshold value stored in the storage unit 93 is determined in advance depending on each dispensing process target and each dispensing amount.

(2-2.1) Statistic Distance

Next, the statistic distance will be described.

The statistic distance is an index obtained by quantifying similarity between two events represented by multiple feature variables. In a case of Embodiment 1, calculation is performed on how far target data is away from a group of known data prepared in advance. Herein, a calculation method of the Mahalanobis distance will be described as an example of the statistic distance.

FIG. 4 is a table schematically illustrating an example of a group of the known data. In the group of the known data, each data of the n (1 to n) number of events has the k (1 to k) number of feature variables (n and k are positive integers).

In order to calculate the Mahalanobis distance, normalization is first performed by using Equation (1) below, when the respective feature variables of the target data are set to $y_1, y_2, \ldots, y_k$, average values of the respective feature variables of known data $x_{nk}$ are set to $z_1, z_2, \ldots, z_k$, and standard deviations are set to $\sigma_1, \sigma_2, \ldots, \sigma_k$.

$$X_i = \frac{y_i - z_i}{\sigma_i} \quad \text{(Equation 1)}$$

However, in Equation (1), a condition is set to $i=1, \ldots, k$.

Then, a Mahalanobis distance $D_M$ of the target data from the group of the known data is expressed by Equation (2) below.

$$D_M = \sqrt{\frac{1}{k}(X_1 \ldots X_k) A \begin{pmatrix} X_1 \\ \vdots \\ X_k \end{pmatrix}} \quad \text{(Equation 2)}$$

As expressed by Equation (2) above, a product of a feature variable matrix of evaluation data and a correlation matrix of the determination-purpose reference data is divided by k, and the square root is calculated, thereby calculating the Mahalanobis distance $D_M$.

In addition to the Mahalanobis distance, the calculation method of the statistic distance which can be applied to Embodiment 1 includes a calculation method of a Euclidean distance, a standard Euclidean distance, a Manhattan distance, a Chebyshev distance, and a Minkowski distance, and multivariate normal density.

(2-2.2) Suitability Verification of Determination-Purpose Reference Data

The determination-purpose reference data used for the abnormality determination process is verified as suitable so that predetermined performance in detecting the abnormal dispensing can be maintained in the determination-purpose reference data suitability verification unit 95. In a case where it is determined as unsuitable for the abnormal dispensing detection, it is determined whether or not component replacement or device adjustment is required.

The suitability of the determination-purpose reference data is verified for anyone of the sample dispensing mechanism 50, the first reagent dispensing mechanism 60, and the second reagent dispensing mechanism 70, as a verification target.

FIG. 5 is a flowchart with regard to a series of processes in the determination-purpose reference data suitability verification unit 95 of the control device 90. FIG. 8 is an internal configuration block diagram of the control device 90, and is a view clearly illustrating a relationship of transmitting an instruction signal and data between internal configuration elements illustrated in FIG. 3.

A series of processes in verifying the suitability of the determination-purpose reference data which is illustrated in FIG. 5 can be performed by an operator or a service engineer through a graphical user interface (GUI) of the control device 90, and is performed independent of a usual analysis operation before the automatic analyzer starts to perform the analysis process. When the device is actuated, the series of processes can also be automatically performed by setting the series of processes in advance.

The series of processes are performed in STEPS 1 to 7 in FIG. 5 by the respective units 93 to 95 and 97 to 99 illustrated in FIG. 8.

In STEP 1 in FIG. 5, channel inner pressure fluctuation data in normal dispensing and abnormal dispensing conditions is acquired. The abnormal dispensing condition described herein includes a case of aspirating bubbles on the liquid level of the specimen or the reagent (bubble aspirating), a case of aspirating only the air (air aspirating), or a case of aspirating the specimen having high viscosity. When the pressure data under the abnormal dispensing condition is acquired, a stopping position of the probe in the vertical direction is controlled in order to realize reliable data acquisition.

When STEP 1 is performed, the specimen or the reagent for verifying the suitability of the determination-purpose reference data is installed in advance in each sample disk or each reagent disk. As the liquid of the specimen or the reagent for verifying the suitability, it is conceivable to use those which simulate the minimum viscosity or the maximum viscosity available in operation, but the liquid is not limited thereto. For example, a dispensing amount serving as a data acquisition target is set to the amount of both ends in switching operation patterns of a syringe drive motor (dispensing amount for 8 times in a case of 4 operation patterns). The normal and abnormal data are acquired for each dispensing amount. In order to improve reliability, two or three sets may be repeated.

FIG. 6 is a view illustrating an example of operation conditions for acquiring the normal and abnormal data used in verifying the suitability of the determination-purpose reference data in STEP 1. As illustrated in FIG. 6, sequence numbers in the condition are 1 to 12. A normal operation is performed in 8 rows, and an abnormal operation (air aspirating) is performed in only 4 rows. A setting amount has 3 types of 10 μL, 49 μL, 50 μL, and 100 μL. An aspirating target (pseudo-reagent) has 2 types of purified water and aqueous solution containing glycerin 30%. Each sequence is performed 5 times.

The aspirated target (pseudo-reagent or pseudo-specimen) is not necessarily discharged to the reaction container 41, and may be discharged to a specific place such as a cleaning tank in a cleaning mechanism.

FIG. 7 illustrates an acquired waveform example of channel inner pressure data in normal and abnormal conditions which are used for verifying the suitability of the determination-purpose reference data in STEP 1. In FIG. 7, a solid line waveform represents an example of a normal case, and a broken line waveform represents an example of an air aspirating (abnormal) case. An aspirating section is approximately 125 ms from when aspirating starts. As illustrated in FIG. 7, in the aspirating section, there is a pressure difference of approximately 2,000 Pa between normal aspirating and abnormal aspirating (air aspirating).

Next, in STEP 2, a feature variable is calculated for a digital signal of a pressure waveform under the normal dispensing and abnormal dispensing conditions, which is a pressure sensor signal sent from the A/D converter 54a by the pressure signal process unit 98 of the control device 90. The feature variable described herein includes a pressure average value at every fixed time interval or appearing timing of a minimum point and a maximum point of pressure fluctuations which appear when the plunger 55 starts to be operated and stops the operation.

Next, in STEP 3, the statistic distance calculation unit 94 calculates a statistic distance $D_M$ between the determination-purpose reference data stored in the storage unit 93 and each data acquired in STEPS 1 and 2.

The determination-purpose reference data includes a normal data set and an abnormal data set, or any one of both data sets. With regard to the acquired normal data, the statistic distance $D_M$ from the normal data set configuring the determination-purpose reference data is calculated. With regard to the acquired abnormal data, the statistic distance $D_M$ from the abnormal data set configuring the reference database is calculated.

The abnormal dispensing determination unit 97 compares the statistic distance $D_M$ calculated by the statistic distance calculation unit 94 with a threshold value stored in the storage unit 93 in advance, and determines whether or not the abnormal dispensing is present.

Next, in STEP 3A, the determination-purpose reference data suitability verification unit 95 determines whether or not the result determined by the abnormal dispensing determination unit 97 coincides with normality or abnormality of the determination-purpose reference data as illustrated in FIG. 6. In a case where both coincide with each other, it is determined that the abnormality detection function is normal, and the result is transmitted to the control instruction unit 99. The control instruction unit 99 switches the automatic analyzer to a standby state. In this case, the control instruction unit 99 can cause the display device 92 to display that the abnormality detection function is normal.

In a case where the result determined by the abnormal dispensing determination unit 97 does not coincide with normality or abnormality of the determination-purpose reference data, the determination-purpose reference data suitability verification unit 95 determines a possibility that the abnormality detection function may not be normal, and transmits the result to the control instruction unit 99. Then, the process proceeds to STEP 4.

In STEP 4, the control instruction unit 99 acquires the determination-purpose reference data. Through the same operation as that in STEP 1, the control instruction unit 99 acquires the data under the normal and abnormal conditions. A dispensing amount of the acquired data can be optionally set. It is possible to set only the dispensing amount of items having an analysis parameter registered therein or only the dispensing amount of selected items. The reference data acquired herein is added to the existing determination-purpose reference data so as to prepare temporary determination-purpose reference data. The prepared temporary determination-purpose reference data is stored in the storage unit 93 via the pressure signal process unit 98.

Without being added to the existing determination-purpose reference data, only the reference data acquired herein can also be used in preparing the temporary determination-purpose reference data. These operations can be automatically performed in such a way that the control instruction unit 99 controls each unit. In STEP 4, the reference data may be prepared by acquiring any one data under the normal condition or under the abnormal condition.

Next, in STEP 5, the statistic distance calculation unit 94 calculates the statistic distance $D_M$ between the data acquired in STEPS 1 and 2 and the temporary determination-purpose reference data prepared in STEP 4. Calculation content is the same as that in STEP 3.

Next, in STEP 5A, the determination-purpose reference data suitability verification unit 95 compares the statistic distance $D_M$ calculated by the statistic distance calculation unit 94 with a threshold value stored in the storage unit 93 in advance. If the difference is smaller than a fixed value, it is determined that the abnormality detection function is normal, and the result is transmitted to the control instruction unit 99. The control instruction unit 99 switches the automatic analyzer to a standby state.

If the above-described difference is equal to or greater than the fixed value, the determination-purpose reference data suitability verification unit 95 determines a possibility that the automatic analyzer may have an abnormal component or that a failure may occur in the automatic analyzer, and transmits the result to the control instruction unit 99.

Next, in STEP 7, the control instruction unit 99 causes the display device 92 to display an alarm so as to urge component replacement or adjustment of the automatic analyzer. Alternatively, the control instruction unit 99 performs the series of processes again from STEP 4, and performs a determination process again so as to determine whether or not the determination is wrong.

Next, an abnormality determination process operation of the dispensing mechanism during an analysis process operation will be described.

(2-2.3) Operation of Abnormality Determination Process

FIG. 9 is an operation flowchart illustrating the abnormality determination process of the dispensing mechanism during the analysis process operation.

Referring to FIG. 9, the operation of the sample dispensing mechanism 50 will be described as an example. The abnormality determination process is similarly performed on the first reagent dispensing mechanism 60 and the second reagent dispensing mechanism 70.

If the input device 91 instructs to start the analysis, the control instruction unit 99 of the control device 90 causes the sample dispensing mechanism 50 to perform an aspirating operation in a dispensing step (STEP 1), and causes the pressure signal process unit 98 to calculates the feature variable of the target data with regard to the digital signal of the pressure waveform of the pressure sensor 54 which is sent from the A/D converter 54a (STEP 2). Subsequently, the statistic distance calculation unit 94 calculates the statistic distance $D_M$ from the determination-purpose reference data which is selected in advance from the target data (STEP 3).

Next, the abnormal dispensing determination unit 97 determines whether or not the statistic distance $D_M$ is smaller than a predetermined threshold value stored in the storage unit 93 (STEP 4). In a case where the determination result is NO in STEP 4, a recovery process is performed (STEP 5), and the process is completed. Here, the recovery process is a process in which the abnormal dispensing determination unit 97 issues information relating to abnormal aspirating, and in which the control instruction unit 99 performs an operation for an alarm process and for proceeding to the subsequent specimen process.

In addition, in a case where the determination result is YES in STEP 4, the drive mechanism 56 and the plunger 55 perform a discharge operation in accordance with the instruction of the control instruction unit 99 (STEP 6), and determines whether or not the subsequent dispensing is to be performed (STEP 7). In STEP 7, in a case where the determination result is YES, that is, in a case where the subsequent dispensing is to be performed, the process returns to the process in STEP 1. In a case where the determination result is NO, that is, in a case where the subsequent dispensing is not to be performed, the process is completed.

Here, the process is similarly performed on the pressure fluctuation during the discharge operation.

(3) Advantageous Effect of Embodiment 1

An advantageous effect according to Embodiment 1 configured as above will be described.

In general, in some cases, due to a time-dependent change or replacement of each component configuring the channel, the output values of the pressure sensor in the automatic analyzer fluctuate even if the same specimen or the same reagent is dispensed. In a case where the fluctuation width is large, the reference database stored in advance is determined as unsuitable through the abnormal dispensing detection in the device, thereby resulting in a problem in that detection performance of the abnormal dispensing becomes poor.

In Embodiment 1, the data is acquired under the predetermined conditions (normal condition and abnormal condition) so as to verify whether or not the determination-purpose reference data stored in the storage unit 93 is suitable for the abnormality detection function to be properly fulfilled. Then, in a case where it is determined that the determination-purpose reference data is not suitable for the abnormality detection function to be properly fulfilled, the temporary determination-purpose reference data is prepared. The prepared temporary determination-purpose reference data is compared with the data previously acquired under the predetermined conditions (normal condition and abnormal condition). In a case where the difference therebetween is greater than the predetermined threshold value, a possibility is determined that the automatic analyzer may have an abnormal component or that a failure may occur in the automatic analyzer, and the result is transmitted to the control instruction unit 99. An alarm is displayed so as to urge component replacement or adjustment of the automatic analyzer. Alternatively, the series of processes is performed again, and a determination process is performed again so as to determine whether or not the determination is wrong.

Therefore, it is possible to realize the automatic analyzer which can accurately detect a state where component replacement or device adjustment is required, without being affected by a time-dependent change or replacement of each component configuring a channel.

Embodiment 2

Next, Embodiment 2 according to the present invention will be described.

Embodiment 1 is an example of the automatic analyzer which can accurately detect a state where the component replacement or the device adjustment is required. In contrast, in addition to this configuration, Embodiment 2 is an example which can improve analysis accuracy by updating the determination-purpose reference data to optimized data and optimizing a function to detect the abnormal dispensing.

In Embodiment 2, an overall configuration of the automatic analyzer, and reagent and sample dispensing mechanisms are the same as those in Embodiment 1. Thus, illustration and detailed description will be omitted.

FIG. 10 is a functional block diagram of the control device 90 according to Embodiment 2. In an example illustrated in FIG. 10, a point different from the functional block diagram illustrated in FIG. 3 according to Embodiment 1 is that the determination reference data updating unit 96 is added to the configuration in the example illustrated in FIG. 3. In Embodiment 2, the control device 90 also includes the analysis process unit 100. In order to simplify the description, illustration will be omitted. The omitted illustration is similarly applied to Embodiments 3 and 4 to be described later.

In addition, FIG. 11 illustrates a flowchart with regard to a series of processes of the control device 90. In FIG. 11, a point different from the flowchart illustrated in FIG. 5 according to Embodiment 1 is that STEP 6 is added to all of STEPS 1 to 3, 3A, 4, 5, 5A, and 7 illustrated in FIG. 5.

In addition, FIG. 12 is an internal configuration block diagram of the control device 90, and is a view clearly illustrating a relationship of transmitting an instruction signal and data between internal configuration elements illustrated in FIG. 10. FIG. 12 corresponds to the internal configuration block diagram in FIG. 8 according to Embodiment 1. In contrast, an example illustrated in FIG. 12 includes the entire example illustrated in FIG. 8. The determination-purpose reference data updating unit 96 is added thereto.

Each operation in STEPS 1 to 3, 3A, 4, 5, 5A, and 7 in FIG. 11 is the same as each operation in Embodiment 1, and thus, description thereof will be omitted. Only items relating to STEP 6 will be described.

In STEP 5A in FIG. 11, the determination-purpose reference data suitability verification unit 95 causes the process to proceed to STEP 6, if a difference between the statistic distance $D_M$ and a threshold value stored in the storage unit 93 in advance is smaller than a fixed value.

In STEP 6, the determination-purpose reference data updating unit 96 instructed by the determination-purpose reference data suitability verification unit 95 to update the determination-purpose reference data updates the temporary determination-purpose reference data prepared in STEP 4 to formal determination-purpose reference data, and stores the formal determination-purpose reference data in the storage unit 93.

An abnormality determination process according to Embodiment 2 is the same as that according to Embodiment 1, and thus, detailed description will be omitted.

According to Embodiment 2 of the present invention, it is possible to obtain the same advantageous effect as that according to Embodiment 1. In addition, Embodiment 2 is configured so that the determination-purpose reference data is updated to optimized data. Accordingly, the abnormal dispensing can be always accurately detected without being affected by a time-dependent change or replacement of each component configuring a channel. Therefore, it is possible to obtain a very reliable analysis result.

Similarly to Embodiment 1, in Embodiment 2, the temporary determination-purpose reference data is also prepared by adding the existing determination-purpose reference data thereto. The prepared temporary determination-purpose reference data is stored in the storage unit 93 via the pressure signal process unit 98. In addition, without being added to the existing determination-purpose reference data, the temporary determination-purpose reference data can also be prepared by using only the reference data acquired herein.

Embodiment 3

Next, Embodiment 3 according to the present invention will be described.

According to Embodiment 3, multiple determination-purpose reference data items are stored in the storage unit 93. During a usual analysis process operation, the determination-purpose reference data item to be used is fixed to one optimized determination-purpose reference data item. When the suitability of the determination-purpose reference data items is verified, in a case where the suitability is denied, the determination-purpose reference data item is updated to an optimized data item out of other determination-purpose reference data items.

Then, according to this example, in a case where the suitability of all multiple determination-purpose reference data items cannot be verified, an alarm is displayed.

In Embodiment 3, the overall configuration of the automatic analyzer, the reagent and sample dispensing mechanisms, and the abnormality process during the analysis operation are the same as those in Embodiment 1. Thus, illustration and detailed description will be omitted.

In addition, the configuration of the control device 90 is the same as that in Embodiment 2. Thus, illustration and detailed description will be omitted.

FIG. 13 is a flowchart with regard to a series of processes in the control device 90 according to Embodiment 3.

STEPS 1 and 2 in FIG. 13 are the same as STEPS 1, 2, and 3 illustrated in FIG. 12 in Embodiment 2.

In STEP 3A in FIG. 13, if the determination is wrong, the process proceeds to STEP 5 so as to determine whether or not a process for verifying the suitability is completed for all of the multiple determination-purpose reference data items. In STEP 5, if the process for verifying the suitability is not completed for all of the multiple determination-purpose reference data items, the process proceeds to STEP 7 so as to acquire the subsequent determination-purpose reference data item stored in the storage unit 93. The subsequent determination-purpose reference data item is set as the temporary determination-purpose reference data item, and the process returns to STEP 3.

In STEP 3A, if the determination is not wrong, the process proceeds to STEP 4. The determination-purpose reference data updating unit 96 updates the temporary determination-purpose reference data item in which the determination is not wrong, as the determination-purpose reference data item, and stores the updated data item in the storage unit 93. The updating described herein includes a case where as long as the determination of the previously used determination-purpose reference data is not wrong, the determination-purpose reference data item is continuously used as the formal the determination-purpose reference data item.

In STEP 5, in a case where all of the determination-purpose reference data items are completed, it means that there is no suitable data item in the multiple determination-purpose reference data items. Accordingly, the process proceeds to STEP 6. The control instruction unit 99 causes the display device 92 to display the component replacement or the device adjustment as an alarm.

According to Embodiment 3, it is also possible to obtain the same advantageous effect as that according to Embodiment 2.

Embodiment 4

Next, Embodiment 4 according to the present invention will be described.

Embodiment 4 is an example in which Embodiment 2 and Embodiment 3 are combined with each other.

FIGS. 14 and 15 are operation flowcharts according to Embodiment 4. FIG. 14 has the same STEPS as STEPS 1 to 3, 3A, 4, 5, and 7 in the flowchart illustrated in FIG. 13 in Embodiment 3.

Then, FIG. 15 illustrates STEPS 8 to 12 subsequent to STEP 5 in FIG. 14. STEPS 8, 9, and 11 in FIG. 15 correspond to STEPS 4, 5, and 5A in FIG. 11 according to Embodiment 2. Furthermore, STEPS 10 and 12 in FIG. 15 correspond to STEPS 6 and 7 in FIG. 11.

Similarly to Embodiment 3, according to Embodiment 4, multiple determination-purpose reference data items are stored in the storage unit 93. During a usual analysis process operation, the determination-purpose reference data item to be used is fixed to one optimized determination-purpose reference data item. When the suitability of the determination-purpose reference data items is verified, in a case where the suitability is affirmative, the determination-purpose reference data item is updated to the affirmative data item.

Then, in Embodiment 4, in a case where the suitability is denied when the suitability of the determination-purpose reference data is verified, similarly to Embodiment 2, the determination-purpose reference data is acquired, and is set to new temporary determination-purpose reference data (STEP 8). Next, in STEP 9, the statistic distance calculation unit 94 calculates the statistic distance $D_M$ between the data acquired in STEPS 1 and 2 and the temporary determination-purpose reference data prepared in STEP 8.

Next, in STEP 11, the determination-purpose reference data suitability verification unit 95 compares the statistic distance $D_M$ calculated by the statistic distance calculation unit 94 with the threshold value stored in the storage unit 93 in advance. If the difference therebetween is smaller than a fixed value, it is determined that the abnormality detection function is normal. The determination-purpose reference data updating unit 96 instructed by the determination-purpose reference data suitability verification unit 95 to update the determination-purpose reference data updates the temporary determination-purpose reference data prepared in STEP 8 to formal determination-purpose reference data, and stores the formal determination-purpose reference data in the storage unit 93.

If the above-described difference is equal to or greater than the fixed value, the determination-purpose reference data suitability verification unit 95 determines a possibility that the automatic analyzer may have an abnormal component or that a failure may occur in the automatic analyzer, and transmits the result to the control instruction unit 99.

Next, in STEP 12, the control instruction unit 99 causes the display device 92 to display an alarm so as to urge component replacement or adjustment of the automatic analyzer. Alternatively, the series of processes from STEP 8 is performed again, and a determination process is performed again so as to determine whether or not the determination is wrong.

In Embodiment 4, the overall configuration of the automatic analyzer, the reagent and sample dispensing mechanisms, and the abnormality process during the analysis operation are the same as those in Embodiment 2. Thus, illustration and detailed description will be omitted.

In addition, the configuration of the control device 90 is also the same as that according to Embodiment 2. Thus, illustration and detailed description will be omitted.

According to Embodiment 4, it is also possible to obtain the same advantageous effect as that according to Embodiment 2.

According to the present invention, the abnormal dispensing can be determined, based on not only an aspirating waveform but also a discharge waveform of the sample or the reagent.

In addition, in the above-described embodiments, the suitability of the determination-purpose reference data is determined by acquiring both data items of the data item in a case of the normal dispensing in STEP 1 in FIGS. 5, 13, and 14 and the pressure data items in a case of the abnormal dispensing. However, the suitability of the determination-purpose reference data can also be determined by acquiring either the data item in the case of the normal dispensing or the pressure data items in the case of the abnormal dispensing.

REFERENCE SIGNS LIST

10 SAMPLE DISK (SAMPLE DISK),
11 SPECIMEN CONTAINER,
12 SPECIMEN CONTAINER RACK,
20 FIRST REAGENT DISK,
21 REAGENT CONTAINER,
30 SECOND REAGENT DISK,
31 REACTION CONTAINER,
40 REACTION DISK,
41 REACTION CONTAINER,
42 STIRRING MECHANISM,
43 CLEANING MECHANISM,
50 SAMPLE DISPENSING MECHANISM,
51 DISPENSING NOZZLE,
52 THROTTLE PORTION,
53 DISPENSING CHANNEL,
54 PRESSURE SENSOR,
55 PLUNGER,
56 DRIVE MECHANISM,
57 METERING PUMP,
58 VALVE,
59 PUMP,
60 FIRST REAGENT DISPENSING MECHANISM,
70 SECOND REAGENT DISPENSING MECHANISM,
80 PHOTOMETRIC MECHANISM,
90 CONTROL DEVICE,
91 INPUT DEVICE,
92 DISPLAY DEVICE,
93 STORAGE UNIT,
94 STATISTIC DISTANCE CALCULATION UNIT,
95 DETERMINATION-PURPOSE REFERENCE DATA SUITABILITY VERIFICATION UNIT,
96 DETERMINATION-PURPOSE REFERENCE DATA UPDATING UNIT,
97 ABNORMAL DISPENSING DETERMINATION UNIT,
98 PRESSURE SIGNAL PROCESS UNIT,
99 CONTROL INSTRUCTION UNIT,
100 ANALYSIS PROCESS UNIT

The invention claimed is:

1. An automatic analyzer comprising:
a dispensing mechanism including a nozzle, a pump, a drive mechanism, and a pressure sensor configured to detect a pressure inside the nozzle, the dispensing mechanism being configured to aspirate and discharge a first dispensing target to a reaction container;
a photometric mechanism configured to emit light and detect light that has been transmitted through a reaction container containing a solution to analyze a specimen contained in the reaction container;
a display;
a storage unit that stores data including first determination-purpose reference data used in determining whether the dispensing mechanism is normal or abnormal; and
a controller connected to the dispensing mechanism, the photometric mechanism, the display, and the storage unit, the controller programmed to:
determine whether a dispensing operation of the dispensing mechanism is abnormal based on the first determination-purpose reference data stored in the storage unit;
control the dispensing mechanism to aspirate and discharge a control substance and acquire and store pressure data detected by the pressure sensor as acquired first pressure data,
calculate a first statistical distance between the stored first determination-purpose reference data and the acquired first pressure data and determine whether the first statistical distance is within a first predetermined threshold,
upon determining the first statistical distance is not within the first predetermined threshold, control the dispensing mechanism to aspirate and discharge the control substance and acquire and store second pressure data detected by the pressure sensor as acquired second pressure data,
calculate second determination-purpose reference data from the acquired second pressure data and store the second determination-purpose reference data in the storage unit,
calculate a second statistical distance between the second determination-purpose reference data and the acquired first pressure data and determine whether the second statistical distance is within a second predetermined threshold,
wherein upon determination that the second statistical distance between the second determination-purpose reference data and the acquired first pressure data exceeds the second predetermined threshold, the controller is programmed to determine that the first determination-purpose reference data is not suitable for use in determining whether the dispensing mechanism is abnormal and to cause an alarm to be displayed on the display, and
wherein upon determination that the second statistical distance is within the second predetermined threshold, the controller is further programmed to determine that the first determination-purpose reference data is suitable for use in determining whether the dispensing mechanism is normal or abnormal.

2. The automatic analyzer according to claim 1, wherein the controller is further programmed to:
wherein in a case where the second statistical distance is determined to be within the second predetermined threshold, the first determination-purpose reference data is updated with the second determination-purpose reference data and stored as updated first determination-purpose reference data in the storage unit for use in determining whether the dispensing mechanism is normal or abnormal.

3. The automatic analyzer according to claim 1,
wherein the second determination-purpose reference data is one of data obtained by adding data newly acquired under a predetermined condition to the stored first determination-purpose reference data and only the newly acquired second determination-purpose reference data.

4. The automatic analyzer according to claim 1, wherein the controller is further programmed to:
calculate a statistical distance between the first determination-purpose reference data stored in the storage unit and a detection result of stored pressure data detected by the pressure sensor which is acquired by dispensing of the dispensing mechanism under a predetermined condition and which is output from the pressure sensor under normal and abnormal conditions.

5. The automatic analyzer according to claim 3,
wherein the controller is further programmed to:
calculate a statistical distance between the first determination-purpose reference data stored in the storage unit and a detection result of stored pressure data detected by the pressure sensor which is acquired by using both normal data and abnormal data which are acquired under a predetermined condition.

6. The automatic analyzer according to claim 4,
wherein the controller is further programmed to:
calculate first statistical distances between the first determination-purpose reference data stored in the storage unit and each of the normal data and the abnormal data and determine whether each of the first statistical distances is respectively within the first predetermined thresholds.

7. The automatic analyzer according to claim 3,
wherein the controller is further programmed to: determine whether or not the dispensing mechanism is abnormal, based on a result of comparing a first statistical distance between a detection result from the pressure sensor in a case where the dispensing mechanism dispenses a dispensing target used for analysis and the first determination-purpose reference data, with a third predetermined threshold value.

8. The automatic analyzer according to claim 4,
wherein the first and second statistical distances are determined by any one of a Mahalanobis distance, a Euclidean distance, a standard Euclidean distance, a Manhattan distance, a Chebyshev distance, and a Minkowski distance.

9. An automatic analyzer comprising:
a dispensing mechanism including a nozzle, a pump, a drive mechanism, and a pressure sensor configured to detect a pressure inside the nozzle, the dispensing mechanism being configured to aspirate and discharge a first dispensing target to a reaction container;
a photometric mechanism configured to emit light and detect light that has been transmitted through a reaction container containing a solution to analyze a specimen contained in the reaction container;
a display;
a storage unit that stores data including multiple items of first determination-purpose reference data used in determining whether the dispensing mechanism is normal or abnormal; and
a controller connected to the dispensing mechanism, the photometric mechanism, the display, and the storage unit, the controller programmed to:
determine whether a dispensing operation of the dispensing mechanism is abnormal based on the first determination-purpose reference data stored in the storage unit;
control the dispensing mechanism to aspirate and discharge a control substance and acquire and store pressure data detected by the pressure sensor as acquired first multiple items of pressure data,
calculate multiple first statistical distances between the stored multiple items of first determination-purpose reference data and the acquired first multiple items of pressure data and determine whether each of the multiple first statistical distances is respectively within first predetermined thresholds,
upon determining any one of the first statistical distances is not within the first predetermined threshold, control the dispensing mechanism to aspirate and discharge the control substance and acquire and store second pressure data detected by the pressure sensor as acquired second multiple items of pressure data,
calculate at least one item of second determination-purpose reference data from the acquired second pressure data that corresponds to the one of the first statistical distances that is determined not to be within the first predetermined threshold, and store the at least one item of second determination-purpose reference data in the storage unit,
calculate a second statistical distance between the at least one item of second determination-purpose reference data and the corresponding one of the acquired first multiple items of pressure data and determine whether the second statistical distance is within a second predetermined threshold,
wherein upon determining that the second statistical distance between the at least one item of second determination-purpose reference data and the corresponding one of the acquired first multiple items of pressure data exceeds the second predetermined threshold, the controller is programmed to determine that the corresponding one of the first determination-purpose reference data is not suitable for use in determining whether the dispensing mechanism is abnormal and to cause an alarm to be displayed on the display, and
wherein upon determining that the second statistical distance is within the second predetermined threshold, the controller is further programmed to be suitable for use in determining whether the dispensing mechanism is normal or abnormal.

10. The automatic analyzer according to claim 9, wherein the controller is further programmed to:
wherein in a case where the second statistical distance is determined to be within the second predetermined threshold, the corresponding one of the first determination-purpose reference data is updated with the at least one item of second determination-purpose reference data and stored as updated first determination-purpose reference data in the storage unit for use in determining whether the dispensing mechanism is normal or abnormal.

* * * * *